United States Patent [19]

Kelman et al.

[11] Patent Number: 5,370,693
[45] Date of Patent: Dec. 6, 1994

[54] ORTHOPEDIC IMPLANT AUGMENTATION AND STABILIZATION DEVICE

[75] Inventors: David C. Kelman, Winona Lake; Donald E. McNulty; Daniel L. Anderson, both of Warsaw, all of Ind.

[73] Assignee: DePuy Inc., Warsaw, Ind.

[21] Appl. No.: 952,921

[22] Filed: Sep. 28, 1992

[51] Int. Cl.⁵ .............................................. A61F 2/28
[52] U.S. Cl. ........................................................ 623/16
[58] Field of Search ...................... 623/16, 17, 18, 19, 623/20, 22, 23

[56] References Cited

U.S. PATENT DOCUMENTS

| | | | |
|---|---|---|---|
| 4,536,894 | 8/1985 | Galante et al. | 623/16 |
| 4,563,778 | 1/1986 | Roche et al. | 623/16 |
| 4,566,138 | 1/1986 | Lewis et al. | 623/16 |
| 4,753,657 | 6/1988 | Lee et al. | 623/16 |
| 4,759,769 | 7/1988 | Hedman et al. | 623/17 |
| 4,883,492 | 1/1989 | Frey et al. | 623/16 |
| 5,019,103 | 5/1991 | Van Zile et al. | 623/23 |
| 5,062,850 | 11/1991 | MacMillan et al. | 623/17 |

OTHER PUBLICATIONS

"Redefining Total Knee System", Genesis TM Total Knee System, Richards Medical Company Brochure, one page, date unknown.
"Case 209: Cruciate Ligament Sacrifice", Genesis TM Total Knee System, Richards Medical Company Brochure, one page, date unknown.
"Customizing in Surgery for Revisions and the Unexpected", Johnson & Johnson Orthopaedics Brochure, one page, date unknown.
"Primary & Revision Components", Genesis TM Total Knee System, Smith & Nephew Richards Inc. Brochure, pp. 1-4, date unknown.
"Genesis TM Total Knee System Revision", Surgical Technique-Total Knee System Revision, Smith & Nephew Richards Inc. Brochure, pp. 29-37, date unknown.
"Genesis TM Total Knee System Posterior-Stabilized", Surgical Technique, Smith & Nephew Richards Inc. Brochure, page 29, date unknown.
"Insall/Burstein ® II Modular Knee System", Zimmer, Inc. Brochure, Rev. 2, 20 pages, 1989-1990.

*Primary Examiner*—David Isabella
*Attorney, Agent, or Firm*—Barnes & Thornburg

[57] ABSTRACT

A prosthesis is provided for replacing a bone surface. The prosthesis includes an implant having a surface for abutting a bone, and an augment configured to be attached to the surface of the implant by bone cement to compensate for bone loss. The augment is formed to include an aperture therein defined by an inner wall. The prosthesis also includes a plastic peg coupled to the implant. The peg is configured to enter the aperture formed in the augment and to engage the inner wall of the augment to retain the augment in a spaced apart relation relative to the implant to permit the implant to be installed onto the bone before the bone cement cures. Alternately, the surface of the implant is formed to include an aperture therein, and a plastic retaining ring located in the aperture formed in the surface of the implant. A metal peg is coupled to the augment. The metal peg is configured to enter the aperture formed in the implant and to engage the plastic retaining ring therein to retain the augment in a spaced apart relation relative to the implant.

23 Claims, 2 Drawing Sheets

ORTHOPEDIC IMPLANT AUGMENTATION AND STABILIZATION DEVICE

BACKGROUND AND SUMMARY OF THE INVENTION

This invention relates to an orthopedic implant augmentation and stabilization device. More particularly, this invention relates to an apparatus which facilitates coupling of an augment to a surface of an orthopedic implant to compensate for bone loss while minimizing surgical time and manufacturing costs.

When installing prosthetic implants to replace joints such as in a total knee replacement operation, it is sometimes necessary to compensate for bone loss which can occur through wear or disease. Bone loss can also be caused by removal of previously installed implants.

It is known to provide spacing wedges or augments to compensate for bone loss and to prevent gaps between the bone and the surfaces of the prosthetic implants installed onto the bone. Current methods which are used to attach augments to the prosthetic implants includes screws, snap-fits, and the use of bone cement. The use of screws to hold the augments in place on the implant results in metal against metal contact. Micromotion between the augment and the implant after installation of the implant can cause metal fretting particles or metallic debris to be produced. This can cause an osteolytic reaction and loosening of the implant. It is also known to provide a snap-fit metal against metal contact. These snap-fit augments are allowed to wobble in place and can also produce metal frettings or metallic debris. In addition, it is known to use metal pegs in combination with bone cement to couple an implant to an augment. However, these known metal pegs also produce metal against metal contact which can cause an osteolytic reaction and loosening of the implant.

It is also known to use bone cement between the augments and the implant. Current systems that use bone cement to secure the augments in place do not use anything other than cement to keep the metallic components separated nor do the current systems provide any means for immediate fixation of the augment to the implant. The components cannot be implanted until the bone cement between the implant and the augment is cured. This results in extending the operating room time for the patient from about 15 minutes to about 45 minutes.

One object of the present invention is to provide an apparatus for attaching augments to implants to compensate for bone loss while minimizing surgical time, manufacturing costs, and the number of components necessary to perform surgery.

Another object of the present invention is to provide an apparatus for initially retaining a metal augment relative to a metal implant without producing any metal against metal contact to permit the implant to be installed onto the bone without waiting for bone cement to cure. In this apparatus, standoff means is provided for separating and positioning the metal augment relative to the metal implant while the bone cement cures, the standoff means comprising plastic means engaging the implant and the augment.

In one embodiment of the present invention, acrylic pegs or conical shapes are coupled to the metal implant via ultrasonic welding, interference fits, threads, or other coupling methods. The acrylic components can be used along with bone cement to secure and stabilize the augment relative to the implant. The acrylic components locate and stabilize augments such as tibial and femoral wedges in place until the bone cement between the two components is cured. Therefore, the components of the present invention provide temporary fixation between the augments and the implants until the bone cement cures. The acrylic pegs of the present invention can also provide temporary positioning of the implant relative to the bone until the bone cement cures between the implant and the bone. The acrylic pegs are used to resist movement during implantation. The acrylic pegs eliminate the metal-to-metal contact which is present in known devices. In addition, the acrylic pegs of the present invention can be easily cut and aid in removal of the device.

In another embodiment of the present invention, metallic pegs or projections are provided on the augment to increase the ability of the pegs to sustain higher shear loads. In this embodiment, the augments are provided with an integral square metal peg formed on top of a cylindrical boss. The square peg is designed to be interference fit with a plastic sleeve which is fitted into a hole formed in the implant to be augmented. The cylindrical boss engages the sleeve to provide a stand off to prevent metal against metal contact between the augment and the implant. The boss region is purposely designed to have a diameter smaller than the outside diameter of the sleeve to ensure that only the plastic sleeve contacts the boss. The square peg permits cement flow past the flat sides of the peg to eliminate the potential for cement pressure to build up and prevent seating of the augment.

According to one aspect of the present invention, a prosthesis is provided for replacing a bone surface. The prosthesis includes an implant having a surface for abutting a bone, and an augment configured to be attached to the surface of the implant by bone cement to compensate for bone loss. The augment is formed to include an aperture therein defined by an inner wall. The prosthesis also includes a plastic peg coupled to the implant. The peg is configured to enter the aperture formed in the augment and to engage the inner wall of the augment to retain the augment in a spaced apart relation relative to the implant to permit the implant to be installed onto the bone before the bone cement cures.

In one illustrated embodiment, the peg includes a generally conically shaped head coupled to the surface of the implant and a body portion extending away from the head of the peg. The head portion of the peg engages the inner wall of the augment to retain the augment relative to the implant.

The body portion of the peg extends through the aperture formed in the augment beyond a bottom surface of the augment opposite from the implant. The peg thereby provides means for aligning the prosthesis relative to the bone.

The prosthesis can include a second plastic peg or standoff means coupled to the implant spaced apart from the first plastic peg. The second plastic peg engages a top surface of the augment to provide a stand off to maintain the surface of the implant spaced apart from the top surface of the augment. Such a plastic peg or standoff means may be placed on the metal augment to engage the metal implant.

In another embodiment of the invention, the implant is formed to include an aperture therein and the peg is press fit into the aperture formed in the surface of the implant to couple the peg to the implant. The peg includes first and second conically shaped sections for engaging the implant and the augment, respectively.

According to another aspect of the invention, a prosthesis is provided for replacing a bone surface. The prosthesis includes an implant having a surface for abutting a bone. The surface of the implant is formed to include an aperture therein. The prosthesis also includes an augment configured to be attached to the surface of the implant by bone cement to compensate for bone loss, and a plastic retaining ring located in the aperture formed in the surface of the implant. The prosthesis further includes a metal peg coupled to the augment. The peg is configured to enter the aperture formed in the implant and to engage the plastic retaining ring therein to retain the augment in a spaced apart relation relative to the implant to permit the implant to be installed onto the bone before the bone cement cures.

In this illustrated embodiment, a boss is formed between the peg and the augment. The boss is configured to engage only a top surface of the plastic retaining ring so that the boss provides a stand off to maintain said spaced apart relation between the augment and the implant. The boss has a generally cylindrical shape. The boss has a predetermined diameter and the plastic retaining ring has a diameter larger than the predetermined diameter of the boss so that the boss only engages the plastic retaining ring.

A plastic peg may be coupled to the implant spaced apart from the aperture for receiving the metal peg if desired. The plastic peg engages a surface of the augment to provide a stand off to help maintain the implant in said spaced apart relation relative to the augment.

Alternately, a plastic peg may be coupled to the augment spaced apart from the metal peg if desired. The plastic peg engages a surface of the implant to provide a stand off to help maintain the implant in said spaced apart relation relative to the augment.

It is understood that the present invention can be used with tibial components, femoral components, or any other type of implant which may require augments. Additional objects, features, and advantages of the invention will become apparent to those skilled in the art upon consideration of the following detailed description of the preferred embodiment exemplifying the best mode of carrying out the invention as presently perceived.

BRIEF DESCRIPTION OF THE DRAWINGS

A detailed description particularly refers to the accompanying figures in which.

DETAILED DESCRIPTION OF THE DRAWINGS

Figure 1:
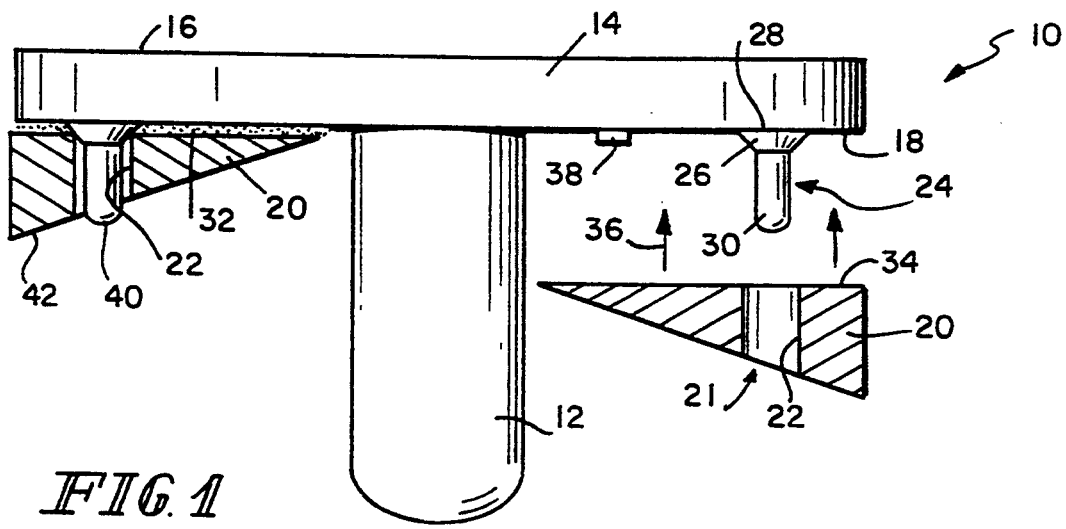
FIG. 1 is a diagrammatical view of a tibial tray including plastic or acrylic pegs secured to a bottom surface of the tibial tray, and an augment for attachment to the bottom surface of the tibial tray to compensate for bone loss.

Referring now to the drawings, FIG. 1 illustrates a tibial prosthetic implant 10 including a stem 12 coupled to a tray 14 in a conventional manner. Tray 14 includes a top surface 16 for receiving a conventional bearing component (not shown) thereon which articulates with a femoral component attached to the resected distal end of the femur. Tibial tray 14 also includes a bottom surface 18 which abuts the resected proximal end of the tibia bone. Tibial component 10 is typically made from a metal material.

Bone loss is often present on the resected end of the bone due to wear or disease. Bone loss can also occur upon removal of a previously installed implant. Therefore, it is often necessary to add metal wedges or augments 20 to prevent gaps between the bone and the implant. It will be understood that augments 20 can have any desired shape. The illustrative augments 20 are formed to include an aperture 21 defined by an inner wall 22. A plastic or acrylic peg 24 is coupled to bottom surface 18 of tibial tray 14. Illustrative peg 24 includes a truncated conical head portion 26 having a flat top surface 28 and a generally cylindrical depending body portion 30 coupled to head 26 opposite from top surface 28. Top surface 28 of peg 24 may be secured to bottom surface 18 of tibial tray 14 by ultrasonic welding. It is understood that peg 24 can be coupled to tibial tray 14 by any suitable manner such as by threads or otherwise.

Bone cement 32 is applied between a top surface 34 of augment 20 and bottom surface 18 of tibial tray 14. The bone cement 32 may be a conventional and well known cement used by orthopedic surgeons to attach components to bones. Augment 20 is installed by moving augment 20 in direction of arrow 36 in FIG. 1 until top surface 34 or inner wall 22 of augment 20 engages the conical section 26 of peg 24 as illustrated in detail in FIG. 2. Peg 24 provides an interference fit with inner wall 22 of augment 20 to retain augment 20 in a spaced apart relation relative to bottom surface 18 of tibial implant 10 until the bone cement 32 between bottom surface 18 of tibial tray 14 and top surface 34 of augment 20 cures. Peg 24 prevents the metal augment 20 from coming into contact with a metal bottom surface 18 of tibial tray 14.

If desired, a second plastic or acrylic peg or standoff means 38 can be coupled to the bottom surface 18 of tibial tray 14 spaced apart from peg 24. Second peg 38 may be smaller than the first peg 24 as illustrated. Second peg 38 provides an extra stand off to help prevent metal surface 18 from engaging metal surface 34. Any desired number of pegs 24 and 38 may be used depending on the application and may be placed on the augment or the implant.

In the illustrative embodiment, after augment 20 is installed over peg 24, a bottom end 40 of peg 24 extends downwardly beyond a bottom surface 42 of augment 20. Therefore, the bottom end 40 of peg 24 may preferably provide temporary positioning of the implant 10 relative to the bone until bone cement between the implant and the bone cures. During installation, bottom end 40 of peg 24 may be aligned with a hole predrilled into the surface of the bone.

Figure 2:
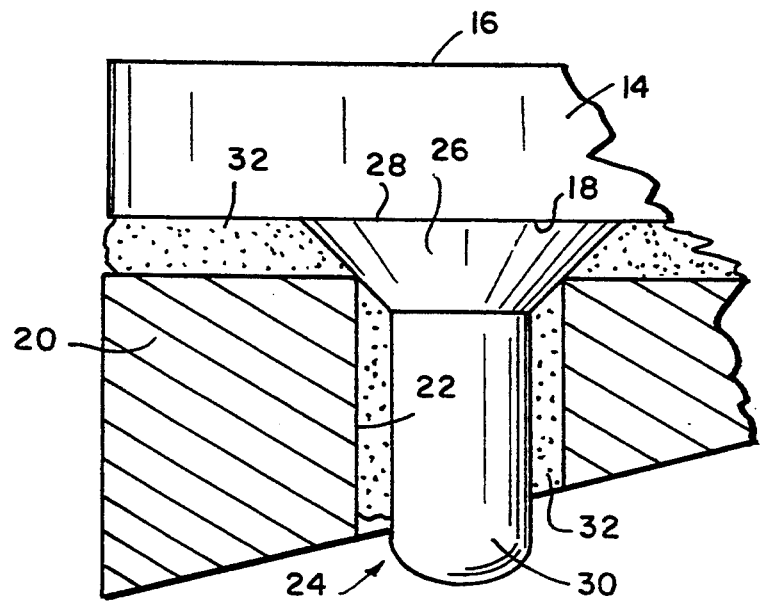
FIG. 2 is an enlarged fragmentary view illustrating the details of the peg coupled to the bottom surface of a tibial tray for stabilizing and temporarily fixing the augment to the tibial tray.

Although the first embodiment illustrated in FIGS. 1 and 2 illustrates the pegs 24 and 38 attached to the implant 10, it is understood that pegs 24 and 38 may be coupled to augment 20 instead. In this instance, an aperture for receiving peg 24 would be formed in bottom surface 18 of implant 10. The illustrative embodiment of the invention may also be used with any type of implant which requires augmentation.

Figure 3:
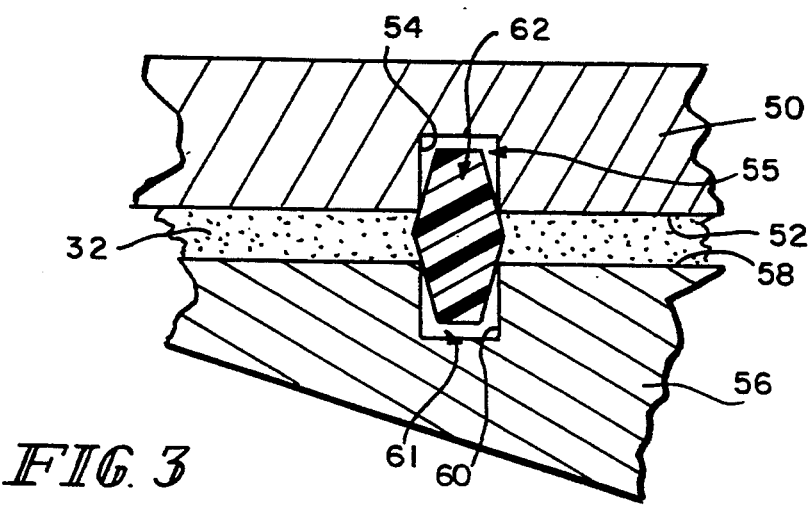
FIG. 3 is a sectional view illustrating another embodiment of the present invention in which a peg is press fit into an aperture formed in the surface of an implant and also press fit into an aperture formed in an augment to temporarily fix the position of the augment relative to the implant.

Another illustrative embodiment of the present invention is illustrated in FIG. 3. In the FIG. 3 embodiment, an implant 50 includes a bottom surface 52. Bottom surface is formed to include an inner wall 54 defining an aperture 55 in the bottom surface 52 of implant 50. An augment 56 is designed to be coupled to bottom surface 52 of implant 50. Augment 56 includes a top surface 58 and an inner wall 60 defining an aperture 61 in top surface 58. Bone cement 32 is applied between bottom surface 52 of implant 50 and top surface 58 of augment 56. A plastic or acrylic peg 62 is press fit into aperture 55 in bottom surface 52 of implant 50 until an outer surface of peg 62 engages the inner wall 54 of implant 50. Peg 62 includes two conically shaped or tapered sections fitting respectively in apertures 55 and 61 to provide the preferred press fit.

Bone cement 32 is then added to implant surface 52. Augment 56 is then installed so that inner wall 60 engages an opposite side outer surface of peg 62 to provide an interference fit. Peg 62 provides spacing between implant 50 and augment 56 so that surface 52 of metal implant 50 does not engage surface 58 of metal augment 56. Peg 62 provides temporary fixation of implant 50 relative to augment 56 until bone cement 32 cures. Implant 50 can be installed onto the bone without waiting for bone cement 32 to cure.

Figure 4:
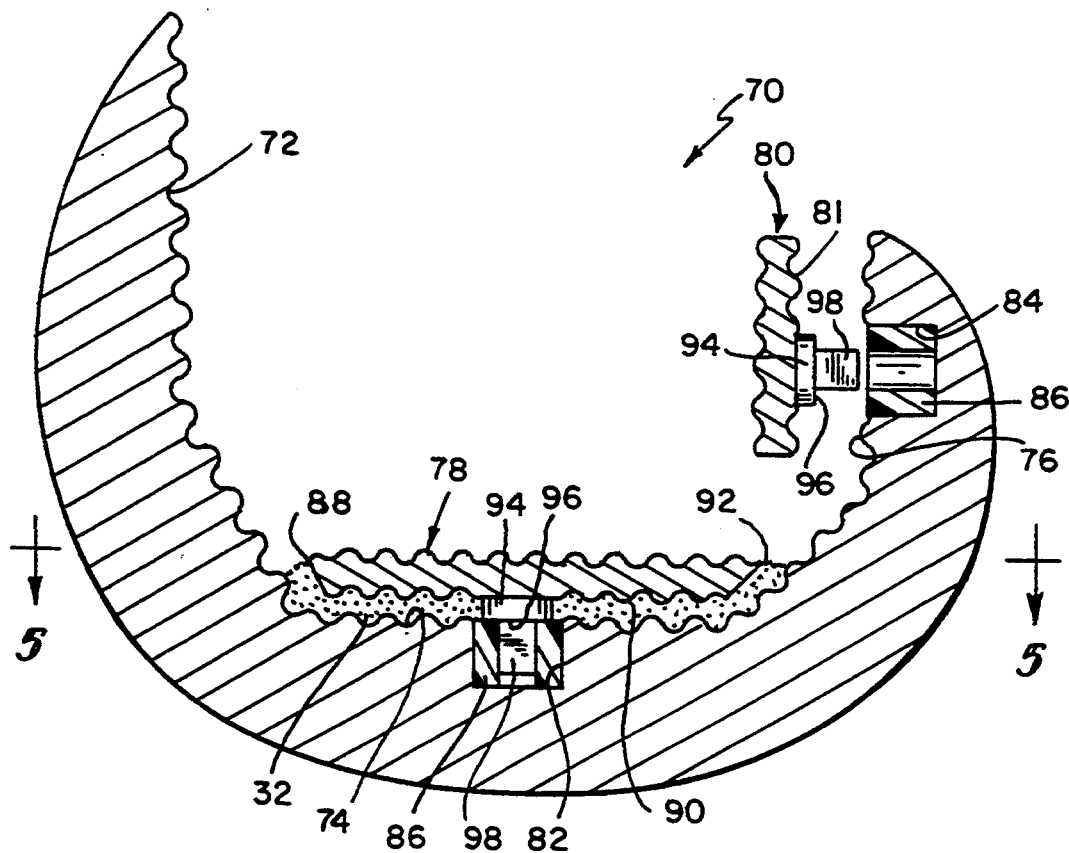
FIG. 4 is a sectional view taken through a femoral condyle component illustrating another embodiment of the augment fixation and stabilization device of the present invention.
Figure 5:
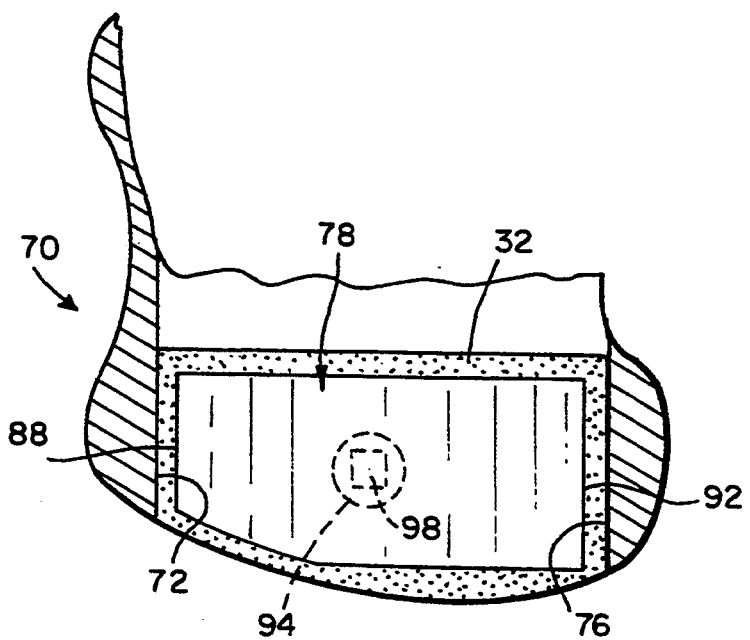
FIG. 5 is a partial sectional view taken along lines 5—5 of FIG. 4.

Another embodiment of the present invention is illustrated in FIGS. 4 and 5. The embodiment illustrated in FIGS. 4 and 5 is illustrated with respect to augments for use with a femoral implant. It is understood, however, that this embodiment of the invention can be used with a tibial implant or any other type of implant in which augmentation is required.

Femoral component 70 illustrated in FIG. 4 includes an anterior surface 72, a distal surface 74, and a posterior surface 76. A distal augment 78 is provided to add to the distal surface 74 to compensate for bone loss. In addition, a posterior augment 80 is provided to add to the posterior surface 76. An anterior augment (not shown) may be provided, if required, to add to anterior surface 72. Implant 70 is illustratively formed to include an aperture 82 in distal surface 74 and an aperture 84 in posterior surface 76. A retaining sleeve 86 is located in each of the apertures 82 and 84. Retaining sleeves 86 may be made from a PMMA or plastic material.

Augment 78 includes an anterior surface 88, a distal surface 90, and a posterior surface 92. Illustratively, anterior and posterior surfaces 88 and 92 are angled at about a 45° angle relative to distal surface 90. Both the bone engaging surfaces of femoral component 70 and the surfaces of augments 78 and 80 have a series of peaks and valleys to increase the surface area of the implant 70 and augments 78 and 80 for receiving bone cement.

A cylindrical boss 94 having a bottom surface 96 is formed on distal surface 90 of augment 78 and on posterior surface 81 of augment 80. A square metal peg 98 extends away from surface 96 of boss 94. Cylindrical boss 94 has an outer diameter less than the outer diameter of retaining sleeve 86 as illustrated in FIG. 4. Therefore, the metal boss 94 only engages the plastic retaining sleeve 86 and not the metal surface of implant 70. Bosses 94 provide a standoffs to maintain augments 78 and 80 spaced apart from distal surface 74 and posterior surface 76, respectively, of implant 70.

Metal peg 98 is illustratively a square peg designed to have an interference fit with retaining sleeve 82. Bone cement 32 is placed between augment 78 and femoral component 70 to secure augment 78 to distal surface 74 of femoral component 70. Bone cement 32 is also placed between posterior surface 82 of augment 80 and posterior surface 76 of implant 70 to secure augment 80 to implant 70. The square peg 98 also permits cement to flow past the flat slides of the peg to eliminate the potential for cement pressure to build up inside apertures 82 and 84 and prevent seating of augments 78 and 80, respectively.

As illustrated in FIG. 5, none of the outer boundary edges of augment 78 touch the metal surfaces of femoral component 70. The only contact between augment 78 and femoral component 70 is between the plastic retaining sleeve 86 and metal boss 94. Metal peg 98 provides temporary retention of augment 78 and 80 relative to femoral component 70 until cement 32 cures. Implant 70 can be installed onto the bone before bone cement 32 cures. The metal pegs 98 projecting from augments 78 and 80 provide increased strength over the plastic pegs illustrated in FIGS. 1-3. Therefore, metal pegs 98 can sustain higher shear loads that may be encountered when seating the implant/augment combination. Metal pegs also will provide higher resistance to shear loads during use.

Plastic pegs such as those illustrated in FIGS. 1-3 may be used with the embodiment of FIGS. 4 and 5 if required. The plastic pegs (not shown) can be coupled to augments 78 or 80 or to implant 70 to provide extra stand offs to help maintain augments 78 and 80 spaced apart from distal surface 74 and posterior surface 76, respectively, of implant 70 until bone cement 32 cures.

Although the invention has been described in detail with reference to a certain illustrative embodiments, variations and modifications exist within the scope and spirit of the invention as described and defined in the following claims.

What is claimed is:

1. A prosthesis for replacing a bone surface, the prosthesis comprising:
    an implant having a surface for abutting a bone;
    an augment configured to be attached to the surface of the implant and disposed between the surface and the bone preventing gaps between the bone and the implant, said augment being attached to the surface by bone cement, the augment being formed to include an aperture therein defined by an inner wall; and
    a plastic peg coupled to the implant, the peg being configured to enter the aperture formed in the augment and to engage the inner wall of the augment to retain the augment in a fixed spaced apart relation relative to the implant to permit the implant to be installed onto the bone before the bone cement cures.

2. The prosthesis of claim 1, wherein the peg includes a generally conically shaped head coupled to the surface of the implant and a body portion extending away from the head of the peg.

3. The prosthesis of claim 2, wherein the body portion of the peg is generally cylindrically shaped.

4. The prosthesis of claim 2, wherein the body portion of the peg has a generally square shaped cross section.

5. The prosthesis of claim 2, wherein the head portion of the peg engages the inner wall of the augment to retain the augment relative to the implant.

6. The prosthesis of claim 2, wherein the body portion of the peg extends through the aperture formed in the augment beyond a bottom surface of the augment opposite from the implant, the peg thereby providing means for aligning the prosthesis relative to the bone.

7. The prosthesis of claim 1, wherein the peg is coupled to the surface of the implant by ultrasonic welding.

8. The prosthesis of claim 1, wherein the implant is formed to include an aperture therein and the peg is press fit into the aperture formed in the surface of the implant to couple the peg to the implant.

9. The prosthesis of claim 8, wherein the peg includes first and second conically shaped sections for engaging the implant and the augment, respectively.

10. The prosthesis of claim 1, further comprising a second plastic peg coupled to the implant spaced apart from the first plastic peg, the second plastic peg engaging a top surface of the augment to provide a stand off to maintain the surface of the implant spaced apart from the top surface of the augment.

11. A prosthesis for replacing a bone surface, the prosthesis comprising:
an implant having a surface for abutting a bone, the implant being formed to include an aperture therein defined by an inner wall;
an augment configured to be attached to the surface of the implant and disposed between the surface and the bone preventing gaps between the bone and the implant, said augment being attached to the surface by bone cement; and
a plastic peg coupled to the augment, the peg being configured to enter the aperture formed in the implant and to engage the inner wall of the implant to retain the augment in a fixed spaced apart relation relative to the implant to permit the implant to be installed onto the bone before the bone cement cures.

12. The prosthesis of claim 11, wherein the peg includes a generally conically shaped head coupled to the augment and a body portion extending away from the head of the peg.

13. The prosthesis of claim 12, wherein the body portion of the peg is generally cylindrically shaped.

14. The prosthesis of claim 12, wherein the body portion of the peg has a generally square shaped cross section.

15. The prosthesis of claim 12, wherein the head portion of the peg engages the inner wall of the implant to retain the augment relative to the implant.

16. The prosthesis of claim 11, wherein the peg is coupled to a surface of the augment by ultrasonic welding.

17. The prosthesis of claim 11, wherein the augment is formed to include an aperture therein and the peg is press fit into the aperture formed in the augment to couple the peg to the implant.

18. The prosthesis of claim 17, wherein the peg includes first and second conically shaped sections for engaging the implant and the augment, respectively.

19. The prosthesis of claim 11, further comprising a second plastic peg coupled to the augment spaced apart from the first plastic peg, the second plastic peg engaging the surface of the implant to provide a stand off to maintain the surface of the implant spaced apart from the top surface of the augment.

20. A prosthesis for replacing a bone surface, the prosthesis comprising:
a metal implant having a surface for abutting a bone;
a metal augment configured to be attached to the surface of the implant and disposed between the surface and the bone preventing gaps between the bone and the implant, said augment being attached to the surface by bone cement;
standoff means for separating said metal implants and metal augments and retain said augment in a fixed spaced apart relation relative to said implant while the bone cement cures, and standoff means comprising plastic means engaging said implant and said augment, said plastic means being configured to prevent metal-to-metal contact in said prosthesis.

21. The prosthesis of claim 20, in which said standoff means is configured as a plastic standoff attached to one of said implant or said augment, and the other of said implants or augments is provided with an aperture for receiving said plastic standoff.

22. The prosthesis of claim 20 in which each of said implant or said augment is provided with an aperture for receiving said plastic means.

23. The prosthesis of claim 20 in which said plastic means comprise a plastic ring imbedded in one of said implant or said augment, said standoff means comprising a boss on the other of said implant or said augment, and a peg extending from said boss into said ring.

* * * * *